(12) United States Patent
Parto et al.

(10) Patent No.: US 9,844,318 B2
(45) Date of Patent: Dec. 19, 2017

(54) DEVICES, SYSTEMS, AND METHODS FOR CALIBRATING AN OCT IMAGING SYSTEM IN A LASER SURGICAL SYSTEM

(71) Applicant: Alcon Research, Ltd., Fort Worth, TX (US)

(72) Inventors: Kambiz Parto, Laguna Hills, CA (US); Barry Wheatley, Oceanside, CA (US); Dean Lin, Chino Hills, CA (US); Tammo Heeren, Aliso Viejo, CA (US); Lingfeng Yu, Rancho Santa Margarita, CA (US)

(73) Assignee: Novartis AG, Basel (CH)

( * ) Notice: Subject to any disclaimer, the term of this patent is extended or adjusted under 35 U.S.C. 154(b) by 99 days.

(21) Appl. No.: 13/850,714

(22) Filed: Mar. 26, 2013

(65) Prior Publication Data
US 2014/0293225 A1 Oct. 2, 2014

(51) Int. Cl.
*A61B 3/10* (2006.01)
*A61F 9/008* (2006.01)

(52) U.S. Cl.
CPC .......... *A61B 3/102* (2013.01); *A61F 9/00821* (2013.01); *A61F 2009/00863* (2013.01); *A61F 2009/00868* (2013.01)

(58) Field of Classification Search
CPC .......... A61B 3/103; A61B 3/14; A61B 3/152; A61B 3/113; A61B 3/107; A61B 3/04;
(Continued)

(56) References Cited

U.S. PATENT DOCUMENTS 5,595,565 A  1/1997 Treat et al.
5,921,981 A  7/1999 Bahmanyar et al.
(Continued)

FOREIGN PATENT DOCUMENTS

EP  0697611 A2  2/1996
JP  10272102 H  10/1998
(Continued)

OTHER PUBLICATIONS

PCT International Search Report for corresponding PCT International Application No. PCT/US2014/031696 dated Aug. 20, 2014, 3 pages.
(Continued)

*Primary Examiner* — Jie Lei
(74) *Attorney, Agent, or Firm* — S. Brannon Latimer

(57) ABSTRACT

An adjustment system for an Optical Coherence Tomography (OCT) imaging system includes an OCT light source; a beam splitter, splitting the OCT light beam into an imaging beam to an imaging arm, and a reference beam to a reference arm; a probe, guiding the imaging beam onto a target and receiving a returned imaging beam from the target; the beam splitter generating an interference beam from the returned imaging beam and a returned reference beam from the reference arm; an imaging detector, detecting the interference beam; an imaging processor, generating an OCT image from the detected interference beam; and an adjustment device, removably coupled to the probe, the adjustment device comprising the target attached to a distal region of a target holder at a working distance from a distal end of the imaging probe, wherein an optical length of the reference arm is adjustable to improve a calibration of the OCT image.

16 Claims, 6 Drawing Sheets

(58) Field of Classification Search
CPC ..... A61B 3/1225; A61B 3/1015; A61B 3/102;
G01B 9/02; G06T 7/0012; A61F 9/00821;
A61F 2009/00868; A61F 2009/00863
USPC ....... 351/205, 206, 208, 210, 212, 216, 221,
351/236, 246; 356/479, 497, 498;
382/131
See application file for complete search history.

(56) References Cited

U.S. PATENT DOCUMENTS

| | | | |
|---|---|---|---|
| 6,004,314 A | 12/1999 | Wei et al. | |
| 6,019,472 A | 2/2000 | Koester et al. | |
| 6,066,128 A | 5/2000 | Bahmanyar et al. | |
| 6,096,028 A | 8/2000 | Bahmanyar et al. | |
| 6,485,413 B1 | 11/2002 | Boppart et al. | |
| 7,261,687 B2 | 8/2007 | Yang | |
| 7,364,543 B2 | 4/2008 | Yang et al. | |
| 7,602,540 B2 | 10/2009 | Masuda et al. | |
| 2001/0036002 A1 | 11/2001 | Fujimoto et al. | |
| 2005/0020926 A1 | 1/2005 | Wiklof et al. | |
| 2006/0132790 A1* | 6/2006 | Gutin .................. | A61B 5/0066 356/479 |
| 2007/0081166 A1 | 4/2007 | Brown et al. | |
| 2007/0265602 A1 | 11/2007 | Morduant et al. | |
| 2008/0051770 A1 | 2/2008 | Scheller et al. | |
| 2008/0304071 A1 | 12/2008 | Kallmann | |
| 2009/0268020 A1 | 10/2009 | Buckland et al. | |
| 2010/0228119 A1 | 9/2010 | Brennan et al. | |
| 2010/0253949 A1 | 10/2010 | Adler et al. | |
| 2011/0001928 A1 | 1/2011 | Sayeram et al. | |
| 2011/0202044 A1 | 8/2011 | Goldshleger et al. | |
| 2012/0033227 A1 | 2/2012 | Bower et al. | |
| 2012/0191078 A1 | 7/2012 | Yadlowsky et al. | |
| 2012/0028123 A1 | 11/2012 | Montgomery et al. | |
| 2013/0003015 A1* | 1/2013 | Kurosaka ............. | A61B 5/0066 351/206 |
| 2013/0038836 A1 | 2/2013 | Smith | |

FOREIGN PATENT DOCUMENTS

| | | |
|---|---|---|
| JP | 2000500043 | 1/2000 |
| JP | 2001515382 | 9/2001 |
| RU | 2288636 C2 | 12/2006 |
| WO | 199717011 | 5/1997 |
| WO | 200042906 | 7/2000 |
| WO | 0172214 A1 | 10/2001 |
| WO | 2010086861 A1 | 8/2010 |
| WO | 2012018796 A2 | 2/2012 |
| WO | 2012166116 A1 | 12/2012 |

OTHER PUBLICATIONS

Han S et al., "Handheld forward-imaging needle endoscope for ophthalmic optical coherence tomography inspection", Journal of Biomedical Optics, Mar./Apr. 2008, vol. 13(2), pp. 020505-1 thru 020505-3.
Wu J et al., "Paired-angle-rotation scanning optical coherence tomography forward-imaging probe", Optics Letters; May 2006, vol. 31, No. 9, pp. 1265-1267.
Yaqoob Z et al., "Methods and application areas of endoscopic optical coherence tomography", Journal of Biomedical Optics 11(6), Nov./Dec. 2006, pp. 063001-1 through 063001-19.
EP14773590.6; Supplementary Partial European Search Report, European Patent Office, dated Aug. 14, 2015, 5 pgs.

* cited by examiner

DEVICES, SYSTEMS, AND METHODS FOR CALIBRATING AN OCT IMAGING SYSTEM IN A LASER SURGICAL SYSTEM

BACKGROUND

Technical Field

Embodiments disclosed herein are related to devices, systems, and methods for adjusting an imaging system in a laser surgical system. In particular, embodiments disclosed herein provide devices, systems and methods that allow for adjusting a reference arm optical path length in an Optical Coherence Tomography (OCT) imaging system of a laser surgical system.

Related Art

The fields of microsurgical and ophthalmic surgical procedures are evolving rapidly. Some of these procedures now involve the use of imaging probes. These imaging can involve fiber-based video imaging, optical coherence tomography (OCT) imaging, and OCT-imaging based computerized operations. To image with high quality and depth resolution, the imaging systems and their imaging depths are to be calibrated with high precision. Precisely calibrated imaging systems can provide accurate images of the tissue being treated or diagnosed with good depth-calibration and good resolution.

One of the problems of calibration is that some portions of the imaging systems, such as their imaging probes, are disposable since they contact the tissue during imaging. Since the optical characteristics vary from probe to probe, for example, because of manufacturing tolerances, the imaging systems may have to be re-calibrated and adjusted for each procedure anew with the new probe. Existing imaging systems do not have a calibrating or adjusting device and thus their depth-calibration and resolution varies from procedure to procedure as the probes get changed.

Accordingly, there is a need for devices, systems, and methods for adjusting ophthalmic imaging systems, such as Optical Coherence Tomography (OCT) imaging systems, alone or in combination with a laser ophthalmic surgical system.

SUMMARY

To provide an adjustment or calibration of imaging systems, consistent with some embodiments, an adjustment device for an imaging system can include a target holder; a coupling mechanism, configured to couple the target holder to an imaging probe; and a target, attached to a distal region of the target holder, wherein the adjustment device is configured to position the target at a working distance from a distal end of the imaging probe.

Consistent with embodiments, an adjustment system for adjusting an optical path length of a reference arm of an Optical Coherence Tomography (OCT) imaging system includes an OCT light source, configured to emit an OCT light beam; a beam splitter, configured to split the OCT light beam into an imaging beam, transferred to an imaging arm, and a reference beam, transferred to a reference arm; a probe, configured to guide the imaging beam onto a target and to receive a returned imaging beam from the target; wherein the beam splitter is configured to generate an interference beam from the returned imaging beam and a returned reference beam from the reference arm; an imaging detector, configured to detect the interference beam; an imaging processor, configured to generate an OCT image from the detected interference beam; and an adjustment device, removably coupled to the probe, the adjustment device comprising the target attached to a distal region of a target holder at a working distance from a distal end of the imaging probe, wherein an optical length of the reference arm is adjustable to improve a calibration of the generated OCT image.

Consistent with embodiments, a method of adjusting a reference arm length of an Optical Coherence Tomography (OCT) system includes generating an OCT light beam by an OCT light source; splitting the OCT light beam by a beam splitter into an imaging beam, transferred to an imaging arm, and into a reference beam, transferred to a reference arm; generating an interference beam from a returned imaging beam from a target through an imaging probe and the imaging arm, and from a returned reference beam from the reference arm; detecting the interference beam by an imaging detector; generating an OCT image from the detected interference beam by an imaging processor; and adjusting an optical length of the reference arm to improve a calibration of the generated OCT image; wherein the target is positioned at a distal region of a target holder at a working distance from a distal end of the imaging probe.

Figure 1:
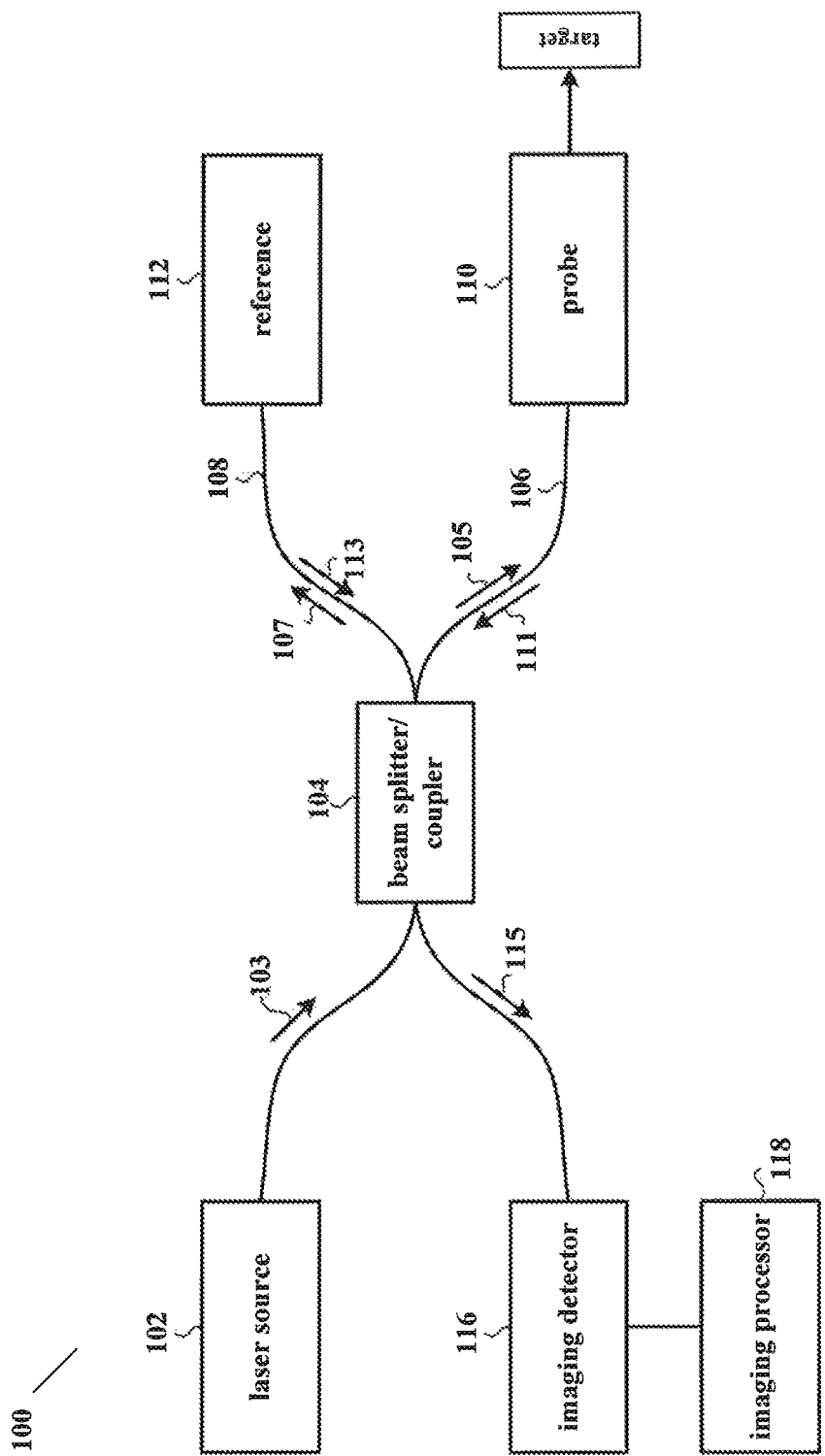
FIG. 1 is a diagram illustrating an Optical Coherence Tomography (OCT) system, consistent with some embodiments.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

Figure 5:
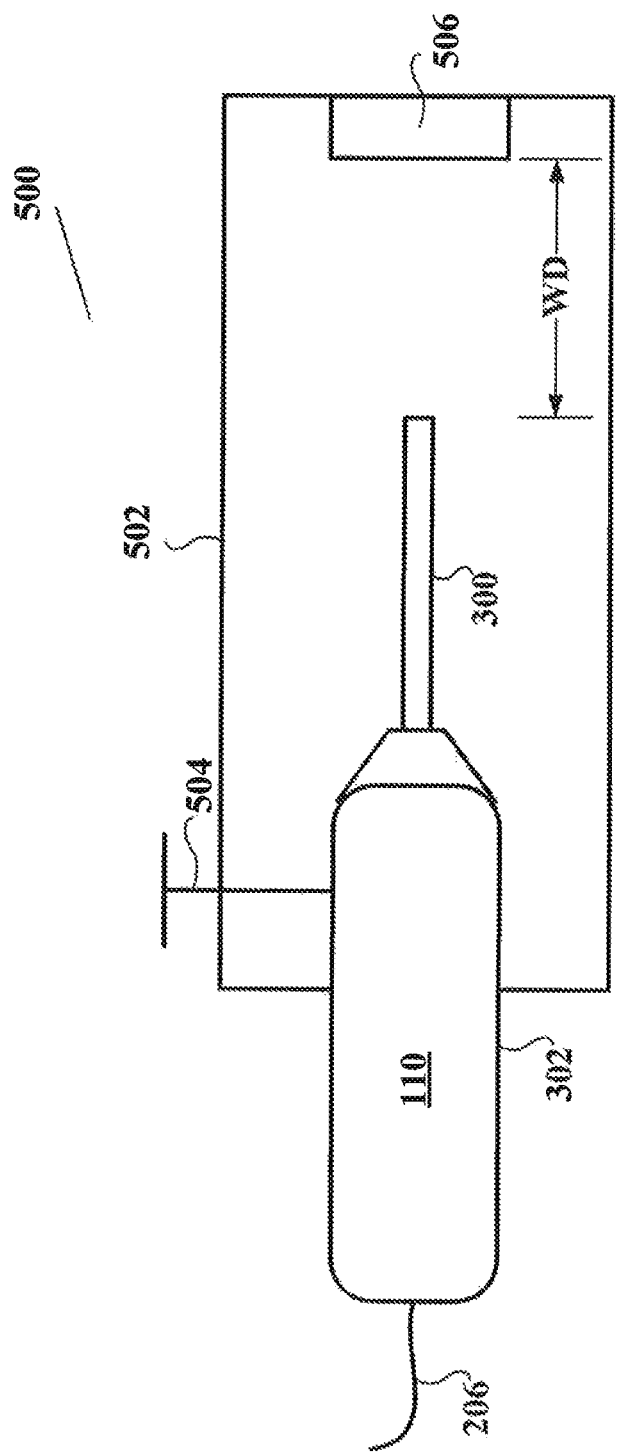
FIG. 5 is a diagram illustrating an adjustment device for adjusting a reference arm optical path length, consistent with some embodiments.
Figure 6:
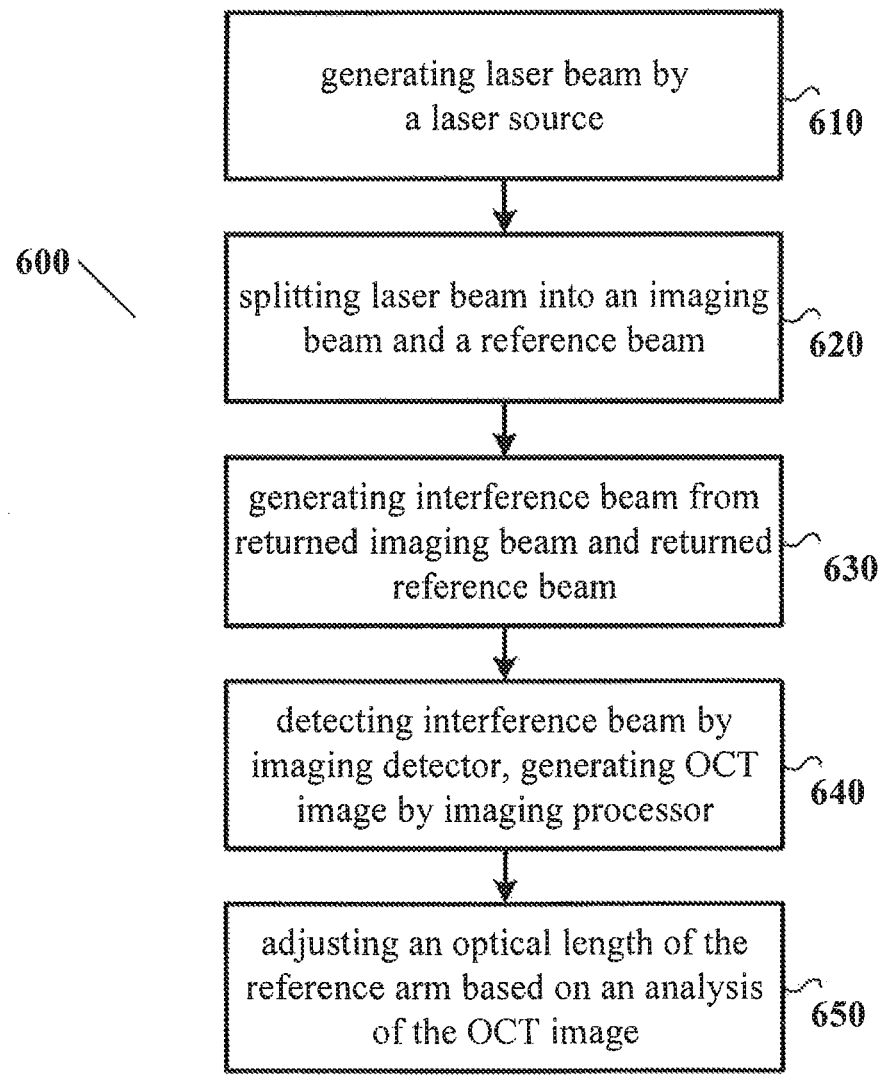
FIG. 6 is a flowchart illustrating a method for adjusting an OCT imaging system using an adjustment device, consistent with some embodiments.

Consistent with some embodiments, there is provided an adjustment or calibration device for adjusting an imaging system. As will be described in detail below, the adjustment device can include a target holder; a coupling mechanism, configured to couple the target holder to an imaging probe; and a target, attached to a distal region of the target holder, wherein the adjustment device is configured to position the target at a working distance from a distal end of the imaging probe. These and other embodiments will be described in further detail below. FIGS. 1-4 illustrate the imaging system associated with the adjustment device, and FIGS. 5-6 illustrate the adjustment device itself.

FIG. 1 illustrates an Optical Coherence Tomography (OCT) imaging system, consistent with some embodiments. OCT is an optical imaging method that is capable of imaging targets in a range of depths and organizing these in-depth images into two- or three-dimensional images with micron-resolution. The possible targets include biological tissues, including the human eye. OCT imaging system 100 can include an OCT light source or laser source 102, configured to emit an OCT light beam 103 to a beam splitter/coupler 104. In some embodiments, the light source 102 can emit a coherent light with a defined spectrum designed according to the requirements of the OCT imaging technique. In some embodiments, the OCT light source 102 can include a super-luminescent diode (SLD), a white light source with a sufficiently broad bandwidth, a swept laser, configured to sweep a sufficiently wide bandwidth or a comb laser with discrete wavelengths. Beam splitter 104 can split the OCT light beam 103 into an imaging beam 105, transferred to an imaging arm 106, and a reference beam 107, transferred to a reference arm 108. Imaging beam 105 can be guided and projected by a probe 110 onto a target, from where it can be returned as a returned imaging beam 111. Reference beam 107 can be guided by reference arm 108 to a reference 112 that can return it as a returned reference beam 113.

Beam splitter 104 can combine the returned imaging beam 111 and the returned reference beam 113 into an interference beam 115. An imaging detector 116 can detect the interference beam 115 and an imaging processor 118 can generate an OCT image from the detected interference beam 113. According to the principles of its operation, the OCT technique uses that portion of the returned imaging beam 111 which is returned from a working distance or depth within the target that has the same optical path length as the returned reference beam 113. Therefore, adjusting the length of the reference arm 108 to select the intended imaging depth or working distance is an important part of calibrating the OCT imaging system 100.

Imaging detector 116 may be a spectrometer with a detector array in a spectrometer based Fourier-Domain OCT imaging system 100, or a photodiode detector in a swept-source Fourier-domain OCT imaging system 100. Consistent with some embodiments, imaging processor 118 may be one or more computing systems including computer-readable media storing instructions for image recognition and processing. The instructions can be executed by one or more processors of the computing systems to process the interference beam 115 detected by imaging detector 116. Imaging processor 118 may also be a microcontroller, application-specific integrated circuit (ASIC), or other programmable device. According to some embodiments, the target may correspond to a tissue in an eye, which may a human eye.

Figure 2:
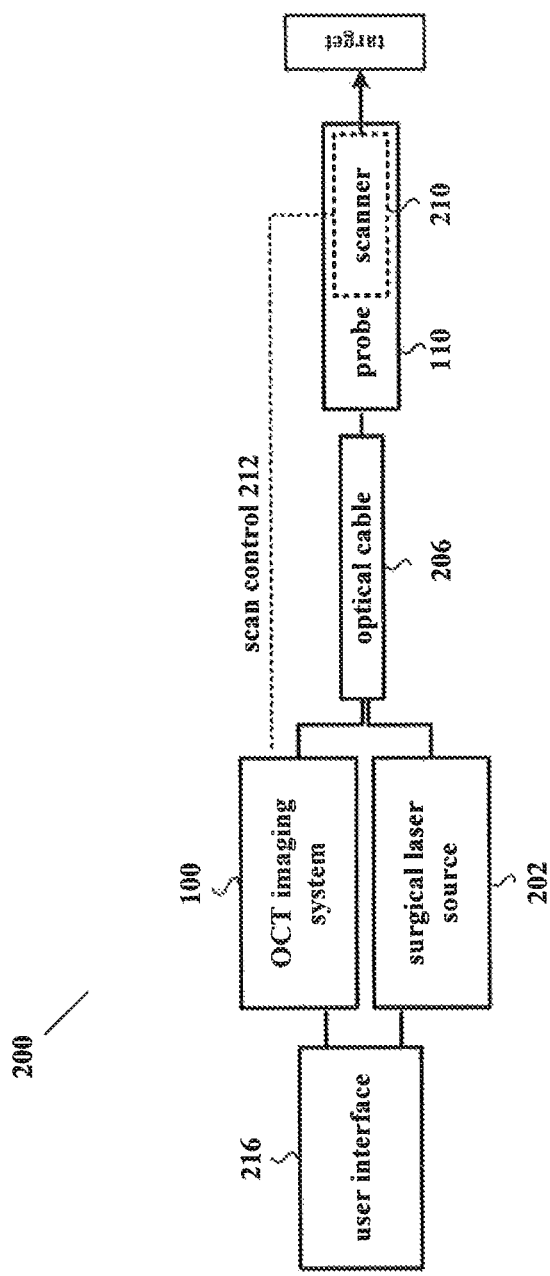
FIG. 2 is a laser surgical system, consistent with some embodiments.

FIG. 2 illustrates a laser surgical system 200, consistent with some embodiments. Laser surgery system 200 can include a surgical laser source 202 and OCT imaging system 100. Surgical laser source 202 can guide a surgical beam into an optical cable 206. OCT imaging system 100 can guide an imaging beam into the same optical cable 206. Optical cable 206 can guide the light beams to probe 110 and thus can be part of imaging arm 106.

OCT imaging systems can be configured to create a one-dimensional image of a depth segment or depth region of the target at individual imaging points by performing a so-called A-scan. Some OCT systems can scan the imaging beam over a sequence of imaging points along a line by a scanning optic or scanner 210, resulting in a sequence of A-scans that can be assembled into a two dimensional image called a B-scan. In these OCT imaging systems, probe 110 may include scanning optic or scanner 210. An OCT imaging system 100 with scanning optic 210 may include scan control line 212, connecting scanning optic or scanner 210 to the OCT imaging system 100. The operation and adjustment of the laser surgical system 200 can be facilitated by a user interface 216.

Optionally, consistent with some embodiments, laser surgical system 200 may also include an illumination source (not shown) to provide visible illumination light to assist the surgeon during the surgery. The illumination source may be any one of numerous surgical illumination sources, such as a xenon lamp, a collection of light emitting diodes, a laser, or any other suitable light source for generating light falling within a visible light spectrum to illuminate a target.

Consistent with some embodiments, surgical laser source 202 may provide one or more beams of laser light having sufficient energy, power or fluence to effect a modification of the targeted tissue, such as effecting a photocoagulation of a targeted retinal tissue. Laser surgical system 200 may include additional surgical laser sources such as laser sources for photocoagulation, trabeculectomy, or other surgical applications, guiding their laser beam into optical cable 206 as well. Laser surgical system 200 may be a system such as described in U.S. patent application Ser. No. 13/354,566 filed on Jan. 20, 2012, which is assigned to the same assignee that this application is subject to assignment to, and is incorporated by reference in its entirety.

Figure 3:
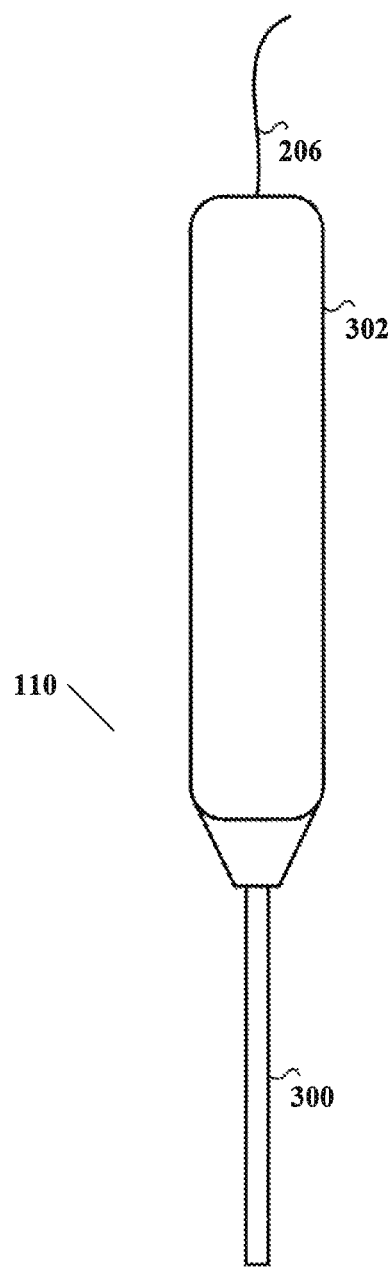
FIG. 3 is a diagram illustrating a probe, consistent with some embodiments.

FIG. 3 is a diagram illustrating a probe, consistent with some embodiments. As shown in FIG. 3, probe 110 can include a cannula assembly 300 and a handpiece or housing 302. According to some embodiments, cannula assembly 300 may have an outer diameter of 300-700 microns, while handpiece or housing 302 may have a substantially larger diameter of 5-20 mm. Handpiece or housing 302 may be adapted for manual operation of probe 110, or for its robotic operation, to be held by an automated device that can be remotely operated. Optical cable 206 may include light-guides, such as optical fibers, carrying light from OCT imaging system 100 and from surgical laser source 202.

In ophthalmic surgical applications, probe 110 may be inserted into the ophthalmic target, such as an eye. The controlling regulatory protocols in many cases require that probe 110 be disposed of after a single use.

Figure 4:
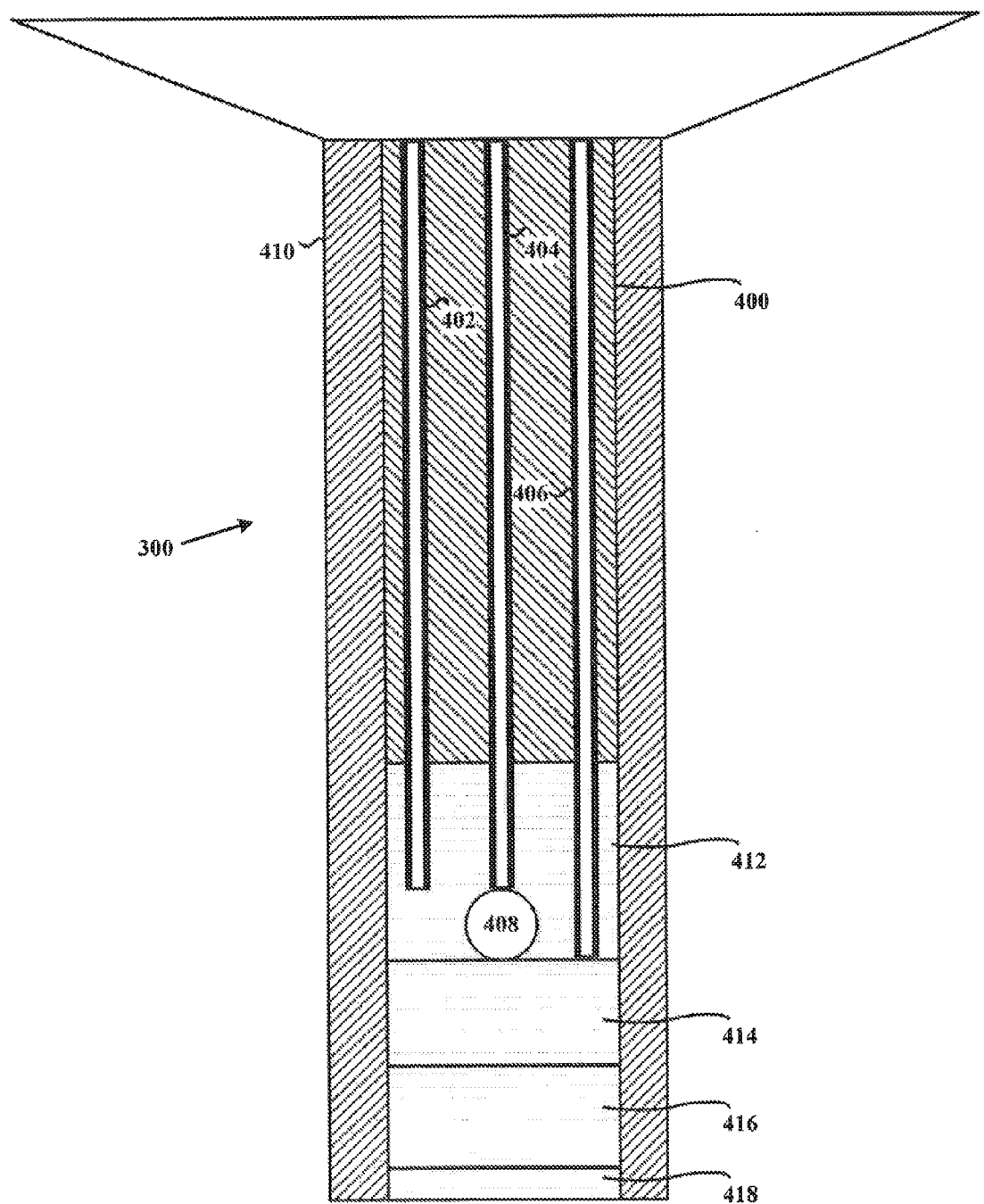
FIG. 4 is a diagram illustrating a cannula assembly for a probe, consistent with some embodiments.

FIG. 4 is a diagram illustrating an embodiment of cannula assembly 300 for probe 110. Cannula assembly 300 can include a fiber bundle 400 that includes an OCT imaging fiber 402, a surgical laser fiber 404, and an illumination fiber 406. Consistent with some embodiments, OCT imaging fiber 402 can be coupled to OCT imaging system 100, surgical laser fiber 404 can be coupled to surgical laser source 202, and illumination fiber 406 can be coupled to an illumination source, all via optical cable 206. Optionally, consistent with some embodiments, surgical laser fiber 404 may be coupled to a ball-lens multi-spot generator 408 which generates multiple spots on a target from the surgical beam transmitted through surgical laser fiber 404. Although a ball-lens multi-spot generator 408 is shown in FIG. 4, in other embodiments fiber bundle 400 may include multiple surgical laser fibers instead of the ball lens 408 for generating multiple spots. In yet other embodiments, cannula assembly 300 may not include multi-spot generator 408.

Consistent with some embodiments, OCT imaging fiber 402 can be a multimode fiber, a fiber bundle, a waveguide, or otherwise may be configured to transmit imaging beam 105 to a target and the returned imaging beam 111, reflected from the target, for detection and processing. Cannula assembly 300 can also include a cannula tube 410 that surrounds fiber bundle 400 and other components of cannula assembly 300. In embodiments that include scanner 210, cannula tube 410 may include two counter-rotating cannulae to carry out the scanning of the imaging beam 105.

Cannula assembly 300 can include a collimating and/or focusing lens 412. Consistent with some embodiments, lens 412 can focus the beams emitted from OCT imaging fiber 402 and from surgical laser fiber 404 to the same plane so that the imaging beam 105 can closely track the surgical beam. In embodiments with scanner 210, cannula assembly 300 can include scanner elements 414 and 416, and a fixed plate 418. Scanner elements 414 and 416 may be gradient index (GRIN) lenses. Scanner elements 414 and 416 can scan imaging beam 105, the surgical beam, and the illumination beam, along lines or circles.

As described earlier, the imaging depth, the performance, and the high resolution of OCT imaging system 100 relies on its calibration: matching the optical path length of reference arm 108 with the optical path length to the target, placed at a working distance from the end of probe 110, through imaging arm 106 and probe 110. Since probe 110 is disposable, before every procedure a new probe is coupled anew to imaging arm 106 and its optical cable 206. Each probe 110 is slightly different, thus the depth-calibration is shifted and the resolution of the OCT imaging system 100 is reduced after the installation of each new probe 110. This undermines the surgeon's ability to aim the surgical beam to its intended depth, as well as lowers the image quality, making the diagnostics of the ophthalmic tissue harder.

Therefore, the performance of OCT imaging system 100 can be improved by a re-calibration after installing each new probe 110, by adjusting the optical path length of reference arm 108 to match the optical path length to the target, placed at a working distance from the end of probe 110. In present systems, there are no trusted methods or systems to perform such a re-calibration and adjustment.

FIG. 5 is a diagram illustrating an adjustment or calibration device for adjusting a reference arm optical path length, consistent with some embodiments. As shown in FIG. 5, an adjustment or calibration device 500 can include a target holder 502, a coupling mechanism 504 to couple target holder 502 to imaging probe 110, and a target 506, attached to a distal region of target holder 502. Adjustment device 500 can be configured to position target 506 at a working distance WD from a distal end of imaging probe 110. The working distance WD can be set to be a typical distance between the distal end of probe 110 and the target tissue during a typical ophthalmic procedure.

In some embodiments, target 506 can include a reflector that can return or reflect imaging beam 105 into imaging arm 106 from the working distance. In some embodiments, target 506 can include a mirror, a corner-cube beam reflector, a coated plate, an attenuator-coated reflector, a target that can provide a lambertian reflection, a diffusive target, a structure with multiple layers, and a structure with a patterned layer. In some embodiments, target 506 can be positioned with a small offset angle or a shift relative to an optical axis of the device 500 to reduce or adjust the intensity of the beam reflected back towards the OCT imaging system 204. In some embodiments, probe 110 can include one or more focusing optical elements, such as lens 412 in FIG. 4, in which case the working distance can be a focal distance of the focusing optical element 412, or in general, a focal distance of the entire OCT imaging system 100.

Coupling mechanism 504 can be a rigid latch, screw, lock, or any equivalent engaging device, capable of holding target holder 502 fixed relative to probe 110 at the working distance WD. Coupling mechanism 504 can lockingly engage any portion of probe 110: the handpiece or housing 302, or the cannula assembly 300.

In some embodiments, coupling mechanism 504 can be configured to allow an adjustment of the position of target 506 to change the working distance, to allow the surgeon to carry out such an adjustment if needed, such as the ophthalmic procedure is to be performed at a different distance.

According to some embodiments, calibration device 500 may be assembled during a manufacture of probe 110 at the factory with the optimal design value of the WD, so that a user of laser surgical system 200 can adjust reference arm 108 while probe 110 is still in its packaging, without being forced to assemble the calibration device 500 and the imaging probe 110.

In other embodiments, adjustment device 500 can be attachable and removable from imaging probe 110. In such embodiments, target holder 502 may be attached to probe 110 using coupling mechanism 504 by a user, such as the surgeon. Such a calibration device 500 can be reusable.

In some embodiments, imaging probe 110 can be part of a separate, self-contained OCT imaging system 100, to be used for a diagnostic process only. In other embodiments, OCT imaging system 100 can be used during laser surgery, but operated separately from the surgical laser probe, to provide imaging information, such as sub-retinal information. In yet other embodiments, imaging probe 110 can be integrated with the laser surgical probe. As described in relation to FIG. 4, in some embodiments a single, fully integrated probe can contain both OCT imaging fiber 402 and surgical laser fiber 404.

In operation, with target holder 502 attached to probe 110, OCT imaging system 100 can generate imaging beam 105 that is transmitted to probe 110 and emitted from OCT imaging fiber 402 of cannula assembly 300 on to target 506. A reflection from target 506 is received by probe 110 and is guided through OCT imaging fiber 402 of cannula assembly 300 back to beam splitter 104, which interferes it with returned reference beam 113 and generates interference beam 115. This interference beam 115 is detected by imaging detector 116. Based on this, imaging processor 118 can generate an OCT image of target 506.

In some embodiments, imaging processor 118 can be configured to determine and to analyze a quality indicator of the generated OCT image. Subsequently, the optical length of reference arm 108 can be adjusted based on the analysis of the quality indicator to improve a calibration of the generated OCT image. The quality indicator can be a wide class of indicators, including a signal-to-noise ratio, a sharpness of a feature of target 506, a spectral property, a phase relation, an interference indicator and a wavefront measure of the OCT image. The improved calibration can be a depth calibration or a resolution of the OCT imaging system 100.

The optical length of reference arm 108 can be adjusted in a single step, or iteratively, the quality indicator being re-measured repeatedly and a convergence of the adjustment process being monitored.

The optical length of reference arm 108 can be adjustable by a system operator using a mechanical, electro-mechanical, electrical, electro-optical or optical adjusting mechanism. The length adjustment can be as simple as moving a reflector in reference 112 at the end of reference arm 108. In other embodiments, it can involve moving a beam splitter along an optical fiber of reference arm 108. In yet other designs, it can involve adjusting an electro-optical actuator, such as a Pockels cell.

In other embodiments, the optical length of reference area 108 can be adjustable by a mechanical, electro-mechanical, electrical, electro-optical and optical automated adjusting system, based on the quality indicator of the generated OCT image. For example, in some designs imaging processor 118 can direct an actuator to adjust a reflector of reference 112 at the end of reference arm 108 to improve the quality indicator of the OCT image and the calibration.

Once the optical length of reference arm 108 has been sufficiently adjusted, the OCT imaging system 100 is ready to produce an image at the desired working depth or distance and with the desired resolution. At this time, calibration or adjustment device 500 may be removed from probe 110 by, for example, loosening coupling mechanism 504. OCT imaging system 100 of laser surgical system 200 may then be ready for performing laser surgery.

Consistent with some embodiments, calibration or adjustment device 500 can be attached to probe 110 during manufacture or fabrication, and can be placed inside the sterile packaging of probe 110. In other embodiments, calibration or adjustment device 500 may be attached to probe 110 while it remains in its sterile packaging. Either of these embodiments allows adjustments to be made to OCT imaging system 100 of laser surgical system 200 without removing probe 110 from the sterile packaging.

FIG. 6 is a flowchart illustrating a method 600 for calibrating or adjusting an OCT imaging system using an adjustment device, consistent with some embodiments. For the purpose of illustration and context, elements of method 600 can be the analogously named elements in any of FIGS. 1-5. As shown in FIG. 6, the method of adjusting a reference arm length of an Optical Coherence Tomography (OCT) system can include in step 610 generating an OCT light beam by a laser source; and in step 620 splitting the OCT light beam by a beam splitter into an imaging beam, transferred to an imaging arm, and into a reference beam, transferred to a reference arm.

The imaging beam can be returned as a returned imaging beam from a target through an imaging probe and the imaging arm. The target can be positioned at a distal region of a target holder at a working distance from a distal end of the imaging probe. The reference beam can be returned as a returned reference beam from the reference arm. Step 630 can include generating an interference beam from the returned imaging beam and from the returned reference beam by the beam splitter.

Step 640 can include detecting the interference beam by an imaging detector, and generating an OCT image from the detected interference beam by an imaging processor.

Step 650 can include adjusting an optical length of the reference arm based on an analysis of the generated OCT image. The analysis can include determining a quality indicator of the OCT image. This adjustment can be carried out to improve a calibration of the OCT imaging system. It can also improve the quality indicator of the generated OCT image. The quality indicator can be a broad class of indicators, including a signal-to-noise ratio, a sharpness of a feature of target, a spectral property, a phase relation, an interference indicator and a wavefront measure of the OCT image. The calibration can include a depth calibration and a resolution.

The adjustment of the optical length of the reference arm can be performed with a mechanical, electromechanical, electrical, electro-optical or optical method.

In some embodiments, the analysis of the OCT image and the adjustment of the optical length can be performed iteratively: after adjusting the optical length of the reference arm to improve the calibration and the quality indicator of the OCT image, the OCT image can be re-analyzed and the quality indicator can be recalculated. With the knowledge of the new, improved quality indicator, the reference arm can be adjusted again to achieve further improvements. These acts can be performed iteratively until a desired calibration or quality indicator is achieved.

The analysis and the determination of the quality indicator may be performed by an operator of the system or may be performed electronically by the imaging processor. In either of these embodiments, when the adjustments of the reference arm achieved the desired calibration or quality indicator for the generated OCT image, the calibrating device can be removed from the imaging probe. The OCT imaging system is then calibrated and ready for use. For example, the OCT imaging system can be part of a laser surgical system to perform ophthalmic surgeries.

It is noted that the target holder can be attached to the imaging probe during or after manufacture. The distance of the target from a distal end of the imaging probe can be a typical imaging depth or working distance, encountered in an ophthalmic surgery. The target holder may also be attached to the imaging probe by a user or operator. In either embodiment, the target holder may be adjustable by the user to adjust the desired working depth between a distal end of the imaging probe and the target.

In particular embodiments, operations of the embodiments may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program.

The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. A disposable calibration device for an Optical Coherence Tomography (OCT) imaging system, the device comprising:
    a target holder comprising a coupling mechanism physically coupling a disposable OCT imaging probe of an imaging arm of the OCT imaging system, which is separate from a reference arm of the OCT imaging system, to the target holder such that the OCT imaging probe is maintained in a fixed position within the target holder; and
    a non-biological reflective target coupled to the target holder, the target positioned within the target holder at a working distance from a distal end of the imaging probe such that an optical path length of the reference arm of the OCT imaging system can be adjusted to correspond to the working distance; wherein:
    the distal end of the imaging probe is configured for insertion into an eye, and the target holder is configured to be removed from the imaging probe prior to insertion of the distal end of the imaging probe into the eye for an imaging procedure; and
    the probe and the target are attached to the target holder and situated inside a sterile package that includes the probe, target, and target holder.

2. The device of claim 1, wherein:
the target comprises a reflector.

3. The device of claim 1, wherein:
the target comprises one of a mirror, a corner-cube beam reflector, a coated plate, an attenuator-coated reflector, a target to provide a lambertian reflection, a diffusive target, a structure with multiple layers, and a structure with a patterned layer.

4. The device of claim 1, wherein:
the target is positioned with at least one of a small offset angle and a small shift relative to an optical axis of the device.

5. The device of claim 1, wherein:
the working distance is a focal distance of the OCT imaging system.

6. The device of claim 1, wherein:
the working distance is adjustable.

7. The device of claim 1, wherein:
the adjustment device is reusable.

8. The device of claim 1, wherein:
the imaging probe is integrated with a surgical probe.

9. An adjustment system for adjusting an optical path length of a reference arm of an Optical Coherence Tomography (OCT) imaging system, comprising:
an OCT light source, configured to emit an OCT light beam;
a beam splitter, configured to split the OCT light beam into an imaging beam, transferred to an imaging arm, and a reference beam, transferred to a reference arm which is separate from the imaging arm of the OCT imaging system;
a disposable imaging probe configured to guide the imaging beam onto a target and to receive a returned imaging beam from the target; wherein
the beam splitter is configured to generate an interference beam from the returned imaging beam and a returned reference beam from the reference arm;
an imaging detector, configured to detect the interference beam;
an imaging processor, configured to generate an OCT image from the detected interference beam; and
a disposable calibration device comprising a target holder to which the imaging probe is removably-coupled such that the imaging probe is maintained in a fixed position within the target holder, the target holder attached to a non-biological reflective target positioned within the target holder at a working distance from a distal end of the imaging probe such that an optical path length of the reference arm can be adjusted to correspond to the working distance and improve a calibration of the generated OCT image; wherein
the distal end of the imaging probe is configured for insertion into an eye;
the target holder is configured to be removed from the imaging probe prior to insertion of the distal end of the imaging probe into the eye for an imaging procedure; and
the probe and the reflective target are attached to the target holder and situated inside a sterile package that includes the probe, reflective target, and target holder.

10. The system of claim 9, wherein:
the working distance is a focal length of the OCT imaging system.

11. The system of claim 9, the target comprising:
at least one of a mirror, a corner-cube beam reflector, a coated plate, an attenuator-coated reflector, a target to provide a lambertian reflection, a diffusive target, a structure with multiple layers, and a structure with a patterned layer.

12. The system of claim 9, wherein:
the target is positioned with at least one of a small offset angle and a small shift relative to an optical axis of the device.

13. The system of claim 9, wherein the target holder comprises a coupling mechanism configured to physically couple the probe to the target holder such that the target is positioned at the working distance from the distal end of the probe.

14. The system of claim 9, wherein:
the imaging processor is configured to determine and to analyze a quality indicator of the generated OCT image; and
the optical length of the reference arm is adjustable based on the analysis of the quality indicator of the generated OCT image.

15. The system of claim 14, wherein:
the optical length of the reference arm is adjustable by a system operator using at least one of a mechanical, electro-mechanical, electrical, electro-optical and optical adjusting mechanism.

16. The system of claim 14, wherein:
the optical length of the reference arm is adjustable by at least one of a mechanical, electro-mechanical, electrical and optical automated adjusting system, based on the quality indicator of the generated OCT image.

* * * * *